(12) United States Patent
Schmotzer et al.

(10) Patent No.: US 6,344,060 B1
(45) Date of Patent: Feb. 5, 2002

(54) KIT FOR IMPLANTING A CEMENTABLE ENDOPROSTHESIS

(75) Inventors: Hans Schmotzer, Kölliken; Christoph Hässig, Küttigen, both of (CH)

(73) Assignee: PLUS Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/762,063

(22) PCT Filed: Aug. 26, 1999

(86) PCT No.: PCT/CH99/00395

§ 371 Date: Mar. 1, 2001

§ 102(e) Date: Mar. 1, 2001

(87) PCT Pub. No.: WO00/15155

PCT Pub. Date: Mar. 23, 2000

(30) Foreign Application Priority Data

Sep. 10, 1998 (EP) .............................. 98810897
Nov. 20, 1998 (EP) .............................. 98122022

(51) Int. Cl.⁷ .................................. A61F 2/32
(52) U.S. Cl. .................. 623/22.12; 623/23.22; 623/23.46; 606/95
(58) Field of Search ............. 623/22.12, 23.22, 623/23.26, 23.27, 23.28, 23.46; 606/92, 85, 99, 95, 100

(56) References Cited

U.S. PATENT DOCUMENTS

| 4,337,773 A | | 7/1982 | Raftopoulos et al. | |
| 4,827,919 A | * | 5/1989 | Barbarito et al. | 623/22.12 |
| 4,997,448 A | | 3/1991 | Filer | |
| 5,047,061 A | * | 9/1991 | Brown | 623/23.22 |
| 5,314,493 A | | 5/1994 | Mikhail | |
| 5,693,099 A | * | 12/1997 | Harle | 623/23.22 |
| 5,755,793 A | | 5/1998 | Smith et al. | |
| 5,792,143 A | | 8/1998 | Samuelson et al. | |
| 5,766,262 A | | 6/1999 | Mikhail | |
| 5,931,871 A | * | 8/1999 | Baur et al. | 623/23.22 |
| 6,179,877 B1 | * | 1/2001 | Burke | 623/22.12 |
| 6,267,785 B1 | * | 7/2001 | Masini | 623/23.22 |

FOREIGN PATENT DOCUMENTS

| DE | 195 18 391 A1 | 11/1996 |
| EP | 0 266 081 | 5/1988 |
| GB | 2 104 390 A | 3/1983 |

* cited by examiner

*Primary Examiner*—Pedro Philogene
(74) *Attorney, Agent, or Firm*—Oliff & Berridge, PLC

(57) ABSTRACT

The kit for implanting a cementable endoprosthesis comprises a fitting instrument (3) and at least two components to be implanted, namely an endoprosthesis shaft (4) and a proximal centering and/or sealing element (1), the shaft (4) and the fitting instrument (3) being designed to be able to be coupled to each other, and the centering and/or sealing element (1) being designed to be placeable on the shaft (4) and to be displaceable in the direction of extension of the latter, and either the fitting instrument (3) comprising a limit stop part (3e) which forms a limit stop relative to the centering and/or sealing element (1), or a marking (6) being arranged on the fitting instrument (3) and on the shaft (4) in order to ensure a defined mutual position between the centering and/or sealing element (1) and the shaft (4).

17 Claims, 3 Drawing Sheets

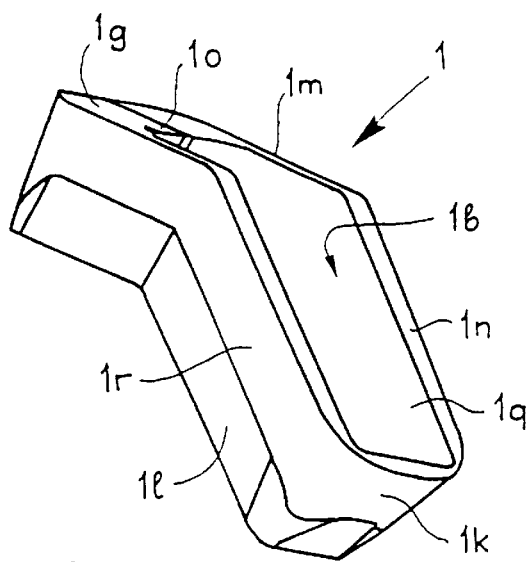
Fig. 1
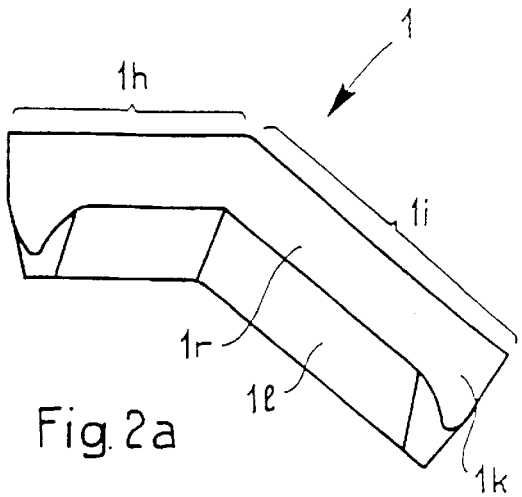
Fig. 2a
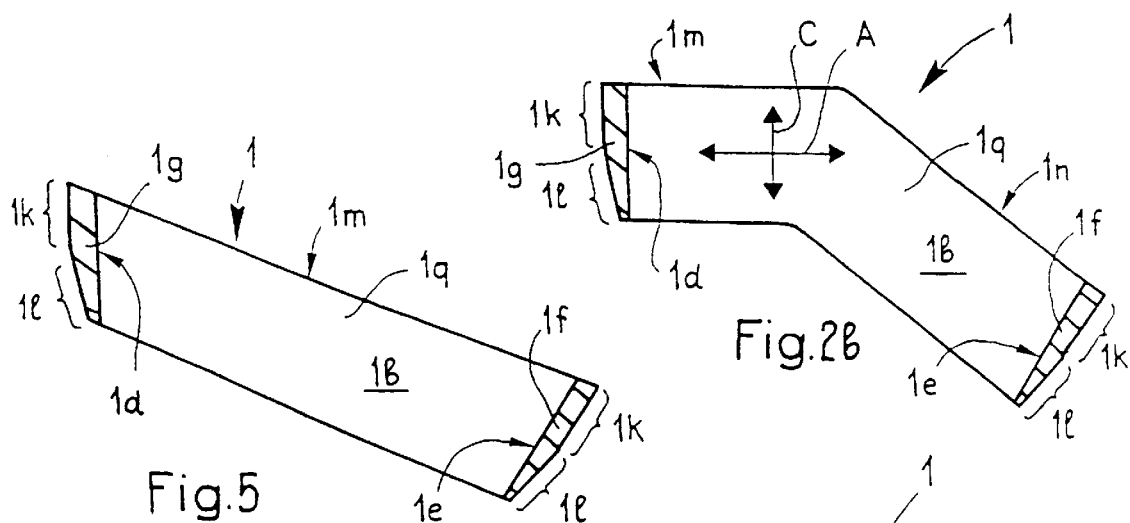
Fig. 5
Fig. 2b
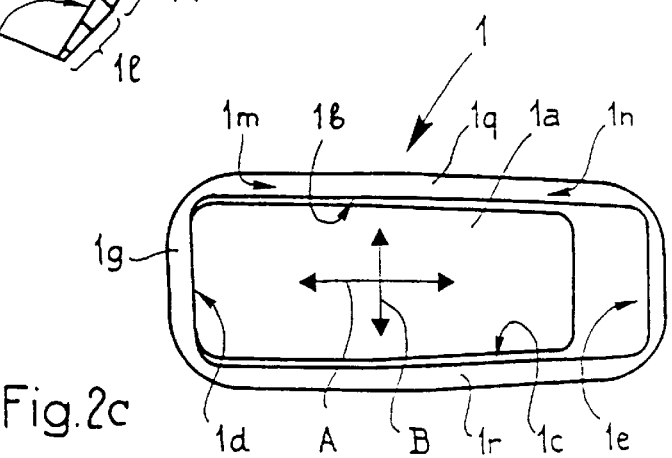
Fig. 2c

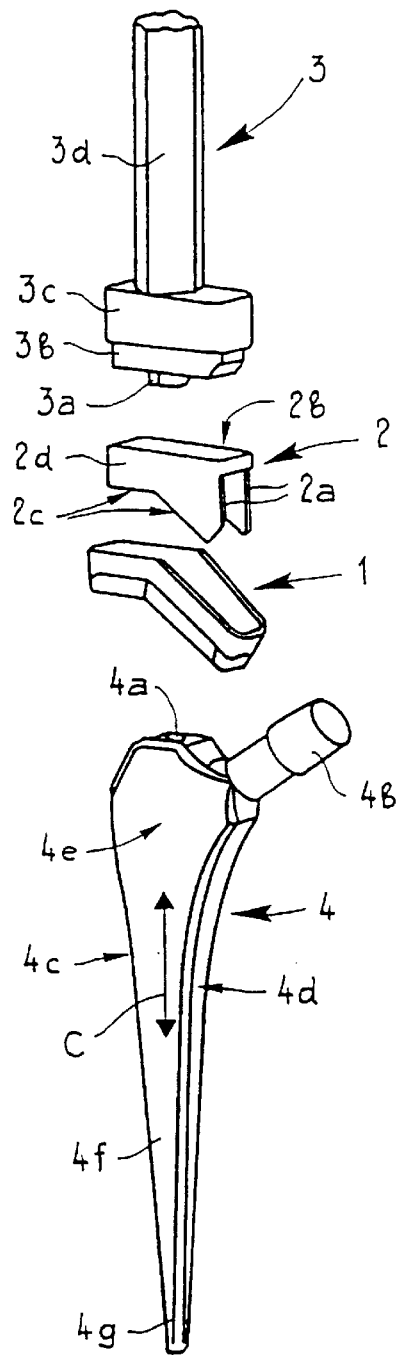
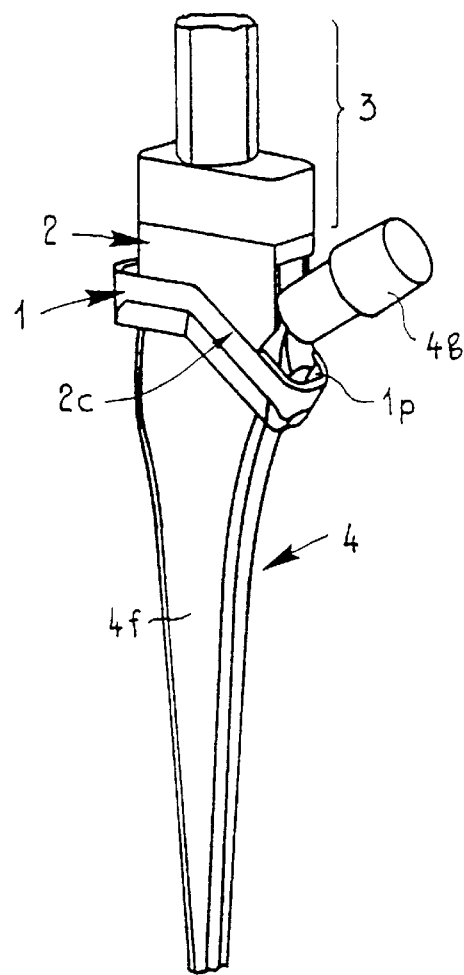
Fig.3
Fig.4

KIT FOR IMPLANTING A CEMENTABLE ENDOPROSTHESIS

FIELD OF THE INVENTION

The invention relates to a kit for implanting a cementable endoprosthesis according to the preamble of claim 1.

BACKGROUND OF THE INVENTION

Document DE 195 18 391 A1 discloses a proximal centering and sealing element for implanting a cementable endoprosthesis shaft, which element on the one hand serves as a proximal centering aid and on the other hand prevents escape of the cement in the proximal direction, as a result of which, when inserting the endoprosthesis shaft into the medullary cavity, there is an increase in the pressure of the bone cement located therein.

This known combination of endoprosthesis shaft and suitably adapted centering and sealing element has the disadvantage that the depth of insertion of the endoprosthesis shaft in the medullary cavity of the femur in the proximal-distal direction can be set only with difficulty and therefore inexactly. In addition, the centering and sealing element has only a limited sealing effect and inadequate centering in the medial-lateral direction.

SUMMARY OF THE INVENTION

The object of the present invention is to make available a set of instruments permitting more precise implantation of a cementable endoprosthesis shaft.

This object is achieved by means of a kit having the features of claim 1. Dependent claims 2 through 17 relate to further advantageous embodiments of this kit.

The object is achieved in particular by means of a kit for implanting a cementable endoprosthesis, comprising a fitting instrument and at least two components to be implanted, namely an endoprosthesis shaft and a proximal centering and/or sealing element, the shaft and the fitting instrument being designed to be able to be coupled to each other, and the centering and/or sealing element being designed to be placeable on the shaft and to be displaceable in the direction of extension of the latter, and either the fitting instrument comprising a limit stop part which forms a limit stop relative to the centering and/or sealing element, or a marking being arranged on the fitting instrument and on the shaft in order to ensure a defined mutual position between the centering and/or sealing element and the shaft.

This embodiment according to the invention has the advantage that the depth of fitting of the endoprosthesis shaft in the medullary cavity of the femur can be adjusted even during implantation. Therefore, it is still possible during implantation to adjust, for example, the length of the femur or depth of fitting of the endoprosthesis shaft in such a way that after the operation has been completed, both legs are the same length. In a preferred embodiment, the kit comprises a manipulating instrument which is inserted into the medullary cavity of the femur before fitting the shaft, in order to determine the optimum depth of fitting, so that in particular an optimum leg length or optimum ligament tensioning is achieved. The optimum depth of fitting which is determined in this way is read off and the endoprosthesis shaft is then inserted into the femur corresponding to this depth of fitting.

The proximal centering and/or sealing element has, in the proximal area of the femur, the task of centering the endoprosthesis shaft in the medullary cavity or sealing off the gap between medullary cavity and shaft, in order to ensure that the bone cement located in the medullary cavity cannot flow out, or of providing centering and sealing at the same time. This centering and sealing element which ensures both centering and sealing is preferably adapted in design to the geometry of the shaft in such a way that a displacement of the shaft along the sealing element in the distal direction is possible while maintaining the sealing effect.

The centering and sealing element can be placed on the resected femoral neck and can be inserted at least partially into the medullary cavity in the proximal area thereof so that the endoprosthesis shaft to be inserted subsequently is inserted in the medullary cavity with all-round centering, the element additionally exerting a sealing effect so that the bone cement located in the medullary cavity is prevented from escaping.

In an advantageous embodiment, the proximal centering and sealing element consists of a sleeve-shaped body extending in a proximal-distal direction, the body having two broad-side boundaries and two narrow-side boundaries which enclose an essentially rectangular inner space, and the two broad-side boundaries each forming inner side surfaces extending essentially parallel in the proximal-distal direction. This centering and sealing element is especially suitable for endoprosthesis shafts of blade-type design whose broad sides extend approximately parallel in the proximal-distal direction. In this way, a particularly good sealing effect is achieved between the centering and sealing element and the endoprosthesis shaft. A centering and/or sealing element is designed as a sleeve-shaped body whose inner space, in an advantageous embodiment, is designed such that a movement of the shaft in the proximal-distal direction is also possible during implantation of the endoprosthesis shaft. If this is desired, then the shaft would be able to settle even some time after implantation since the movement in the proximal-distal direction is not impeded.

The centering and/or sealing element advantageously consists of a polymerized bone cement, in particular polymethyl methacrylate (PMMA). During implantation, this centering and/or sealing element binds chemically to the bone cement present to form a particularly homogeneous connection. However, the centering and/or sealing element can also consist of another material, in particular of a metal such as a biocompatible titanium alloy.

The centering and/or sealing element satisfies either a centering or a sealing function, or both functions simultaneously, said functions being:
- to center the shaft in the proximal section of the medullary cavity;
- to guide the shaft centrally in the proximal-distal direction during fitting of the shaft;
- to prevent tilting in the medial-lateral direction and also twisting of the shaft;
- to seal off the gap occurring between the shaft and the femur in the proximal area so that pressure is exerted on the bone cement located in the medullary cavity.

The centering and/or sealing element has, in the proximal direction, an end face which is advantageously used as a reference surface. The centering and/or sealing element is preferably inserted into the medullary cavity in such a way that said reference surface is flush with the resected surface of the femoral neck. The endoprosthesis shaft is secured on a fitting instrument prior to insertion, a spacer element additionally being secured on the fitting instrument, said spacer element being designed in such a way that with the endoprosthesis shaft inserted deep in the medullary cavity, it lies on the reference surface of the centering and/or sealing element and prevents any further insertion of the shaft. By means of this spacer element which is available in different sizes, the depth of fitting of the endoprosthesis shaft can be adjusted exactly with respect to the resected surface. A spacer element corresponding to the desired depth of fitting is chosen and is secured on the fitting instrument prior to insertion of the endoprosthesis shaft.

A kit is understood as comprising the mutually adapted parts of centering and/or sealing element, endoprosthesis shaft and fitting instrument, if appropriate in combination with one or more spacer elements, and of this kit only the centering and/or sealing element and the endoprosthesis shaft are intended to remain as implants in the body.

A number of illustrative embodiments of the invention are described below with reference to figures, in which:

BRIEF DESCRIPTION OF THE DRAWINGS

FIG. 1 shows a perspective view of a proximal centering and/or sealing element;

FIG. 2a shows a side view of a further proximal centering and/or sealing element;

FIG. 2b shows a cross section through the element according to FIG. 2a;

FIG. 2c shows a top view of the element according to FIG. 2a;

FIG. 3 shows a kit comprising a fitting instrument, a centering and/or sealing element, a spacer element and a shaft;

FIG. 4 shows a shaft which has been inserted with a fitting instrument according to FIG. 3;

FIG. 5 shows a cross section through a further illustrative embodiment of a centering and/or sealing element;

DESCRIPTION OF THE PREFERRED EMBODIMENTS

Figure 6:
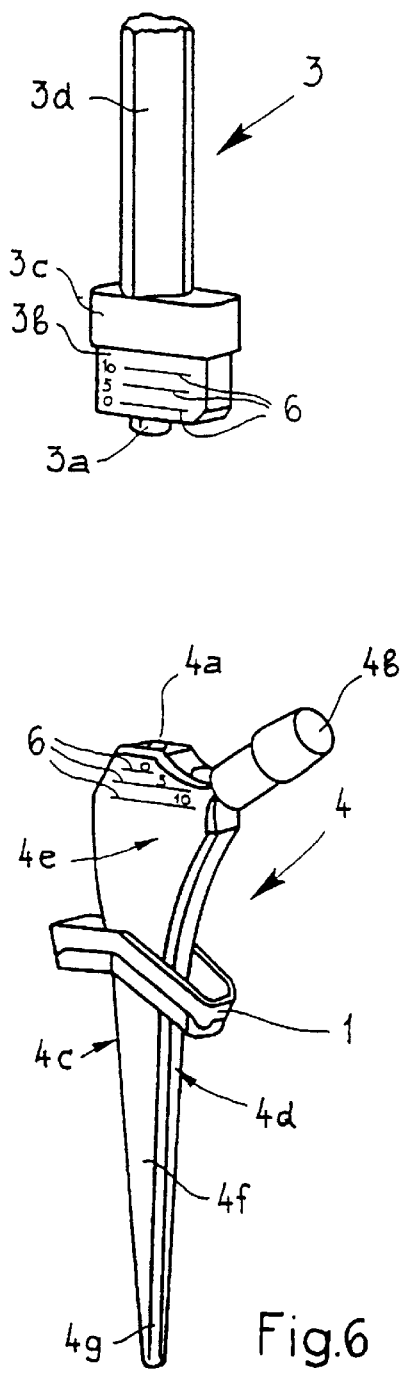
FIG. 6 shows a further kit comprising a fitting instrument, a centering and/or sealing element and a shaft.

FIG. 3 shows an illustrative embodiment of a kit according to the invention, comprising an endoprosthesis shaft 4 which is designed as a straight shaft, the actual shaft 4f having an essentially rectangular cross section with two narrow-side surfaces 4c, 4d and two broad-side surfaces 4e. At the proximal end, the shaft 4f has an internal thread 4a and a cone 4b for a joint head. The kit further comprises a fitting instrument 3 which has a connection rod 3d on which a stamp 3c is secured which opens into an adapter piece 3b and an external thread 3a. The kit further comprises a spacer element 2 which is designed as a sleeve-shaped, rectangular body 2d, with two side wings 2a which form an upper limit stop surface 2b and a lower limit stop surface 2c. The kit also comprises a proximal centering and/or sealing element 1. The spacer element 2 is designed in such a way that it lies with its upper limit stop surface 2b on the stamp 3c. Upon insertion of the endoprosthesis shaft 4, the lower limit stop surface 2c comes to lie at some time on the reference surface 1m, 1n of the proximal centering and/or sealing element 1 and thereby limits, in the direction of extension of the shaft, the mutual positioning of endoprosthesis shaft 4 and centering and/or sealing element 1. Since the centering and/or sealing element 1 lies with its surface 1m, 1n preferably flush with the resected surface of the femur during implantation, the depth of fitting of the shaft 4f is determined by the spacer element 2. A selection of spacer elements 2 are available to the operating surgeon, said spacer elements 2 being designed with different lengths in the proximal-distal direction C. The spacer element 2 represented in FIGS. 3 and 4 is to be regarded as only one illustrative embodiment from a large number of possible designs. The object of the spacer element 2 is to provide an upper and a lower limit stop 2b, 2c in order to ensure a defined depth of fitting of the shaft 4 with respect to the proximal centering and/or sealing element 1 or its reference surface 1m, 1n. This function can be satisfied by spacer elements 2 of widely different designs.

FIG. 4 shows an endoprosthesis shaft 4 in the inserted position, the femur not being represented. After inserting a manipulating shaft into the medullary cavity, the operating surgeon determines the depth of insertion of the shaft with respect to the resection plane. From the plurality of spacer elements, the operating surgeon selects the one which ensures the intended depth of insertion. This selected spacer element 2 is secured on the stamp 3c of the fitting instrument 3, and the endoprosthesis shaft 4 is then screwed onto the external thread 3a via the internal thread 4a. The centering and/or sealing element 1 is then pushed onto the shaft 4f from the distal direction. The endoprosthesis shaft 4 together with the centering and/or sealing element 1, as is represented in FIG. 4, is then inserted into the medullary cavity until the spacer element 2 abuts the proximal centering and/or sealing element 1 and as far as the resection plane which forms a reference plane. The bone cement located in the medullary cavity is thereby compressed and forced out from the medullary cavity toward the centering and/or sealing element 1. At least the inner side surfaces 1b, 1c, 1d lie on the endoprosthesis shaft 4 and exert a sealing action. As long as the endoprosthesis shaft 4 does not lie with its side surface 4d on the inner side surface 1e, a gap 1p is formed between these surfaces, through which gap the bone cement can escape. An operating surgeon can cover this gap 1p, for example with his finger, and can thus control the escape of the bone cement relatively precisely by pressing his finger against the gap 1p or uncovering said gap. The inner side surface 1e can also be arranged with respect to the side surface 4d, or the shaft 4 can be pushed deep into the centering and/or sealing element 1, in such a way that a sealing effect is achieved between these two surfaces 1e, 4d, so that the element 1 acts simultaneously as centering and sealing element. In a preferred embodiment, the centering and/or sealing element 1 is designed, and the bone cement selected, in such a way that said bone cement flows all round the proximal centering and/or sealing element, the bone cement being forced out between the inner side surfaces 1b, 1c, 1d, 1e and the shaft 4a and also between the outer surface of the centering and/or sealing element 1 and the femur.

An illustrative embodiment of the centering and/or sealing element is described with reference to FIGS. 2a through 2c. The centering and/or sealing element consists of a sleeve-shaped body extending in a proximal-distal direction C, said body having two broad-side boundaries 1q, 1r and two narrow-side boundaries 1f, 1g which, as can be seen from the view according to FIG. 2c, enclose an essentially rectangular inner space 1a. The inner side surfaces 1b, 1c of the broad-side boundaries 1q, 1r are designed extending essentially parallel to the proximal-distal direction C and also parallel to the lateral-medial direction A. In the illustrative embodiment shown, as can be seen from FIG. 2c, the inner side surface 1d of the narrow-side boundary 1g extends parallel to the proximal-distal direction C. The broad-side inner side surfaces 1b, 1c could also be designed extending parallel to the proximal-distal direction C, but in the illustrative embodiment shown they converge slightly in the distal direction, this having the advantage of affording an improved sealing effect between endoprosthesis shaft 4 and inner side surface 1b, 1c. The second narrow-side boundary 1f has an inner side surface 1e extending at an inclination to the inner side surface 1d.

In the illustrative embodiment shown, all the boundaries 1q, 1r, 1f, 1g have a part section 1l which extends in the proximal-distal direction C and which forms, adjacent to the part section 1k, a wall thickness tapering in the distal direction, as can be seen in particular from the cross section shown in FIG. 2b. In the proximal direction, the broad-side boundaries 1q, 1r end in a reference surface 1m, 1n. This reference surface 1m, 1n, extending in the medial-lateral direction A, has, as can be seen from FIGS. 2a and 2b, a course which is bent so as to follow the course of the broad-side boundary 1r.

In contrast to the illustrative embodiment according to FIGS. 2a through 2c, the otherwise identically designed body 1 shown in FIG. 5 has two broad-side boundaries 1r, 1q which are rectilinear, i.e. they have no bend point.

In contrast to the illustrative embodiment according to FIGS. 2a through 2c, the body 1 shown in FIG. 1 has a narrow-side boundary 1g which is designed wider in the medial-lateral direction A and which additionally has in the center a continuous gap 10 extending in the proximal-distal direction C.

The endoprosthesis is implanted, for example, as follows:

The femoral neck is resected. The medullary cavity is then widened using a bone rasp. The outer shape of the centering element, i.e. the outer surfaces 1r, 1k, preferably corresponds to the outer shape of the bone rasp. A manipulating shaft is then inserted into the widened medullary cavity and a joint head is fitted onto this manipulating shaft. The bone rasp can if necessary also be designed to receive a joint head or can comprise a joint head and can therefore be left for the time being in the medullary cavity. The position of the joint head is then checked and the leg manipulated, for example in order to examine the leg length, and the depth of fitting of the manipulating shaft or bone rasp can be adjusted in particular in the proximal-distal direction C until an optimum position has been found for the leg. The depth of fitting of the manipulating shaft or bone rasp is then read off. The manipulating shaft or bone rasp is then removed from the medullary cavity, whereupon the bone cement is filled into the medullary cavity. Then, as is represented in FIG. 6, the centering and/or sealing element 1 is pushed over the tip of the shaft 4f, the shaft is secured on the fitting instrument 3, if appropriate using spacer elements 2 determining the depth of fitting, as shown in FIG. 3 or FIG. 4, whereupon the shaft is inserted into the medullary cavity. The centering and/or sealing element 1 is likewise introduced into the medullary cavity. The tapering part section 1l facilitates reliable and centered insertion of the centering and/or sealing element 1 into the medullary cavity. The centering and/or sealing element 1 is pressed in so that the end faces 1m, in preferably are flush with the resected surface, whereupon the shaft is inserted further until the predetermined depth of fitting is reached. The fitting instrument 3 and the optionally used spacer element 2 are then removed.

In the illustrative embodiment shown, as can be seen from FIG. 2c, the narrow-side inner side surface 1d is designed extending in the proximal-distal direction C, the advantage of which is that this surface serves as a bearing and reference surface during insertion of the shaft 4f, said surface 1d causing no displacement of the shaft 4f in the medial-lateral direction A.

A distal centering element can also be arranged on the shaft tip 4g.

To achieve a sealing effect, it is necessary that the inner side surfaces 1b, 1c, 1d, 1e of the centering and/or sealing element 1 are designed to match the geometry of the shaft 4f, so as to achieve a sealing effect. For this reason, these inner side surfaces 1b, 1c, 1d, 1e, predetermined by the shape of the corresponding shaft 4f, can be designed in very different configurations in such a way that a sealing effect between shaft 4f and centering and/or sealing element 1 is achieved with at the same time mutual displaceability in the proximal-distal direction C.

FIG. 6 shows an illustrative embodiment of a kit which comprises an endoprosthesis shaft 4, a distal centering and/or sealing element 1 and a fitting instrument 3. Markings 6 are arranged on the shaft 4 in order to indicate the depth of fitting with numbers "0", "5" and "10". The fitting instrument 3 also has markings 6 with the same numbers. During implantation, the optimum depth of fitting is determined with a manipulating instrument, markings and numbers being arranged on the manipulating instrument. The marking lying at the resected surface is read off. The centering and/or sealing element is then anchored with its upper edge 1m, 1n flush with the resected surface in the medullary cavity and the bone cement is inserted into the medullary cavity. The shaft 4 is then secured on the fitting instrument 3 and introduced into the medullary cavity. During insertion, the operating surgeon can use the markings 6 to accurately determine the depth of insertion of the shaft 4 with respect to the upper edge 1m, 1n of the centering and/or sealing element.

Figure 7:
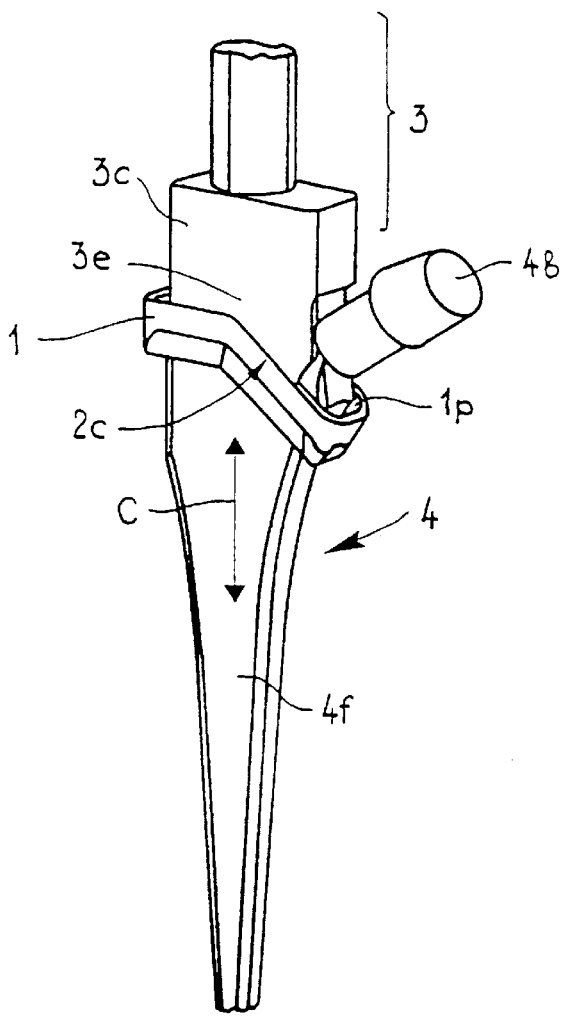
FIG. 7 shows a further kit comprising a fitting instrument, a centering and/or sealing element and a shaft.

FIG. 7 shows a further illustrative embodiment of a kit which comprises an endoprosthesis shaft 4, a distal centering and/or sealing element 1 and a fitting instrument 3. The stamp 3c comprises a securely connected limit stop part 3e which has a limit stop surface 2c for abutting the centering and spacer element 1. Stamps 3c with limit stop parts 3e of different lengths in direction C can be provided, so that the mutual position of centering and/or sealing element 1 and shaft 4 can be set by appropriate choice of stamp 3c.

What is claimed is:

1. A kit for implanting a cementable endoprosthesis, comprising a fitting instrument (3) and at least two components to be implanted, namely an endoprosthesis shaft (4) and a proximal centering and/or sealing element (1), the shaft (4) and the fitting instrument (3) being designed to be able to be coupled to each other, and the centering and/or sealing element (1) being designed to be placeable on the shaft (4) and to be displaceable in the direction of extension of the latter, and either the fitting instrument (3) comprising a limit stop part (3e) which forms a limit stop relative to the centering and/or sealing element (1), or a marking (6) being arranged on the fitting instrument (3) and on the shaft (4) in order to ensure a defined mutual position between the centering and/or sealing element (1) and the shaft (4).

2. The kit as claimed in claim 1, wherein the limit stop part (3e) is designed as a separate spacer element (2).

3. The kit as claimed in claim 2, wherein the spacer element (2) is designed as a sleeve-shaped body (2d).

4. The kit as claimed in claim 2, wherein the spacer element (2) is designed as a preferably rectangular body (2d) whose broad-side boundaries (2a) form a limit stop (2c) oriented toward the centering and/or sealing element (1).

5. The kit as claimed in claim 2, wherein a plurality of spacer elements (2) are provided which are designed with different lengths in the direction of extension of the shaft (4).

6. The kit as claimed in claim 1, wherein the limit stop part (3e) is a constituent part of the fitting instrument (3), and in particular is connected securely thereto.

7. The kit as claimed in claim 1, wherein the centering and/or sealing element consists of a sleeve-shaped body (1) extending in a proximal-distal direction (C), and wherein the body (1) has an inner space (1a) with boundaries (1b, 1c, 1d, 1e) pointing toward the shaft (4) designed in such a way that at least three of the boundaries (1b, 1c, 1d, 1e) bearing on the shaft (4f) exert a sealing effect in the proximal-distal direction (C).

8. The kit as claimed in claim 1, wherein the centering and/or sealing element consists of a sleeve-shaped body (1) extending in a proximal-distal direction (C), wherein the body (1) comprises two broad-side boundaries (1q, 1r) and two narrow-side boundaries (1f, 1g) which enclose an essentially rectangular inner space (1a), and wherein the two broad-side boundaries (1q, 1r) each form an inner side surface (1b, 1c) extending essentially parallel in the proximal-distal direction (C).

9. The kit as claimed in claim 8, wherein at least the broad-side boundaries (1q, 1r) form a part section (1l) which extends in the proximal-distal direction (C) and which has a wall thickness tapering in the distal reaction.

10. The kit as claimed in claim 7, wherein at least the broad-side boundaries (1q, 1r) each have an end face pointing in the proximal direction and forming a reference surface (1m, 1n).

11. The kit as claimed in claim 10, wherein the reference surface (1m, 1n) is designed with a bend in the medial-lateral direction (A).

12. The kit as claimed in claim 7, wherein the element (1) consists of a compacted bone cement, in particular polymethyl methacrylate (PMMA), or of metal, in particular a titanium compound.

13. The kit as claimed in claim 7, wherein the medial, narrow-side boundary (1g) has an inner side surface (1d) extending in the proximal-distal direction (C) and/or a gap (1o) extending in the proximal-distal direction (C).

14. The kit as claimed in claim 7, wherein the broad-side inner side surfaces (1b, 1c) converge slightly in the distal direction.

15. The kit as claimed in claim 1, comprising a manipulating instrument which is designed for insertion into the medullary cavity of the femur and which makes it possible to determine the depth of insertion of the shaft (4) into the medullary cavity.

16. The kit as claimed in claim 15, wherein the manipulating instrument has a shaft with markings arranged thereon in such a way that when the manipulating instrument shaft is inserted into the femur, the depth of insertion can be read off relative to the resected surface of the femur.

17. The kit as claimed in claim 1, wherein the manipulating instrument comprises a bone rasp.

* * * * *